United States Patent
Lunman et al.

(10) Patent No.: US 9,675,726 B2
(45) Date of Patent: Jun. 13, 2017

(54) SCALABLE AIRBORNE PATHOGEN REMOVAL SYSTEM

(71) Applicants: Kyler Lunman, Fernandina Beach, FL (US); Raymond Viggiano, Rumson, NJ (US)

(72) Inventors: Kyler Lunman, Fernandina Beach, FL (US); Raymond Viggiano, Rumson, NJ (US)

(*) Notice: Subject to any disclaimer, the term of this patent is extended or adjusted under 35 U.S.C. 154(b) by 0 days.

(21) Appl. No.: 15/002,668

(22) Filed: Jan. 21, 2016

(65) Prior Publication Data

US 2016/0213803 A1 Jul. 28, 2016

Related U.S. Application Data

(60) Provisional application No. 62/106,393, filed on Jan. 22, 2015.

(51) Int. Cl.
*A61L 9/20* (2006.01)
*A61L 9/00* (2006.01)

(52) U.S. Cl.
CPC ............. *A61L 9/20* (2013.01); *A61L 2209/16* (2013.01)

(58) Field of Classification Search
CPC . A61L 9/20; A61L 2/00; A61L 2/0029; A61L 2/0041; A61L 2/08; A61L 2/10; A61L 19/00; A61L 19/16; A61L 19/18
USPC ...... 422/22, 24; 250/453.11, 454.11, 455.11, 250/493.1, 504 R
See application file for complete search history.

(56) References Cited

U.S. PATENT DOCUMENTS

| | | |
|---|---|---|
| 5,933,702 A | 8/1999 | Goswami |
| 6,855,295 B2 | 2/2005 | Kulp |
| 7,238,326 B2 | 7/2007 | Zhang |
| 7,740,686 B2 | 6/2010 | Metteer |
| 7,875,247 B2 | 1/2011 | Clark et al. |
| 8,350,228 B2 | 1/2013 | Welker |
| 8,404,186 B2 | 3/2013 | Clark et al. |
| 8,845,782 B2 | 9/2014 | Metteer |
| 8,900,518 B2 | 12/2014 | Seck |
| 2006/0177356 A1 | 8/2006 | Miller |
| 2007/0220851 A1 | 9/2007 | Parker et al. |
| 2012/0145693 A1* | 6/2012 | Deng ............... F24H 3/006 219/201 |

(Continued)

*Primary Examiner* — Nicole Ippolito
(74) *Attorney, Agent, or Firm* — PatentFile, LLC; Bradley C. Fach; Steven R. Kick

(57) ABSTRACT

In some embodiments, a scalable airborne pathogen removal system may comprise a housing having an airspace inlet which may be configured to receive air; a supplemental inlet located proximate to the airspace inlet configured to receive supplemental air; and an airspace outlet configured to communicate air from the housing into the airspace. The housing may include a treatment chamber in fluid communication with the airspace inlet, supplemental inlet, and airspace outlet. A first baffle may be positioned within the housing between the airspace inlet and the treatment chamber. Supplemental air from the supplemental inlet may be communicated into the treatment chamber through the first baffle. An ultraviolet light may be disposed within the treatment chamber. An air motivator may be positioned between the treatment chamber and the airspace outlet which may be configured to pull air from the airspace inlet and supplemental inlet through the treatment chamber.

19 Claims, 8 Drawing Sheets

(56) References Cited

U.S. PATENT DOCUMENTS

2013/0239803 A1 9/2013 Palmer
2014/0205504 A1* 7/2014 Khoshbin .............. C01B 13/10
　　　　　　　　　　　　　　　　　　　　　　422/108

* cited by examiner

SCALABLE AIRBORNE PATHOGEN REMOVAL SYSTEM

CROSS REFERENCE TO RELATED APPLICATIONS

This application claims priority to and the benefit of the filing date of U.S. Provisional Application No. 62/106,393, filed on Jan. 22, 2015, entitled "FORCED AIR DUCTED AND SCALABLE ULTRAVIOLET GERMICIDAL IRRADIATION AIRBORNE PATHOGEN REMOVAL SYSTEM", which is hereby incorporated by reference in its entirety.

FIELD OF THE INVENTION

This patent specification relates to the field of airborne pathogen removal. More specifically, this patent specification relates to airborne pathogen removal systems that dilute carbon dioxide ($CO_2$) and remove airborne mold spores and are scalable to accommodate a plurality of different sized airspaces.

BACKGROUND

There are generally four main types of UV air treatment. A first type comprises airstream disinfection via in-duct and/or air handling units in the HVAC system. A second type includes Recirculation units (free standing) that consist of ultraviolet light (UV) lamps and fixtures in a housing. A third type includes Upper-Room Systems which consist of multiple UV lamps hung from the ceiling or walls which are shrouded from the people below because humans cannot tolerate direct exposure to UVC. Finally, a fourth type comprises Barrier Systems which are normally hung in the overhead portion of the door with louvers to constrain the UVC rays.

However, these types of UV air treatment have drawbacks which limit their application. Recirculation units are comparatively smaller and normally sit in a corner of a room or area thereby treating very small areas. Upper room and Barrier types normally have no ability to control or direct airflow either to or away from their unit. In many of these systems the areas have to be evacuated for them to be utilized. Additionally, these UV air treatment types are not scalable so they are unable to irradiate airborne and surface pathogens in different sized areas or airspaces.

Therefore, a need exists for novel systems and methods configured for the irradiation of airborne and surface pathogens using ultraviolet light. There also exists a need for novel ultraviolet germicidal irradiation (UVGI) airborne pathogen removal air movement systems which can be installed anywhere. Finally, there exists a need for novel scalable ultraviolet germicidal irradiation airborne pathogen removal air movement systems.

BRIEF SUMMARY OF THE INVENTION

A scalable airborne pathogen removal system for removing pathogens from an airspace is provided. In some embodiments, the system may comprise a housing having an upstream end and a downstream end. The housing may have an airspace inlet at the upstream end which may be configured to receive air from the airspace; a supplemental inlet located proximate to the airspace inlet at the upstream end with the supplemental inlet configured to receive supplemental air; and an airspace outlet configured to communicate air from the housing into the airspace. A treatment chamber within the housing may be in fluid communication with the airspace inlet, supplemental inlet, and said airspace outlet. A first baffle may be positioned at the upstream end of the housing between the airspace inlet and the treatment chamber. Supplemental air from the supplemental inlet may be communicated into the treatment chamber through the first baffle. An ultraviolet light may be disposed within the treatment chamber. An air motivator may be positioned between the treatment chamber and the airspace outlet at the downstream end of the housing which may be configured to pull air from the airspace inlet and supplemental inlet through the treatment chamber and out of the system through an airspace outlet.

In further embodiments, the system may comprise a second baffle positioned at the downstream end of the housing between the treatment chamber and the air motivator.

In still further embodiments, the first baffle may comprise a first upper incidence surface coupled to a first lower incidence surface. Preferably, the first upper incidence surface may be angularly coupled to the first lower incidence surface at an angle between 20 and 70 degrees.

In even further embodiments, the second baffle may comprise a second upper incidence surface angularly coupled to a second lower incidence surface. Preferably, the second upper incidence surface may be angularly coupled to the second lower incidence surface at an angle between 20 and 70 degrees.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Figure 1:
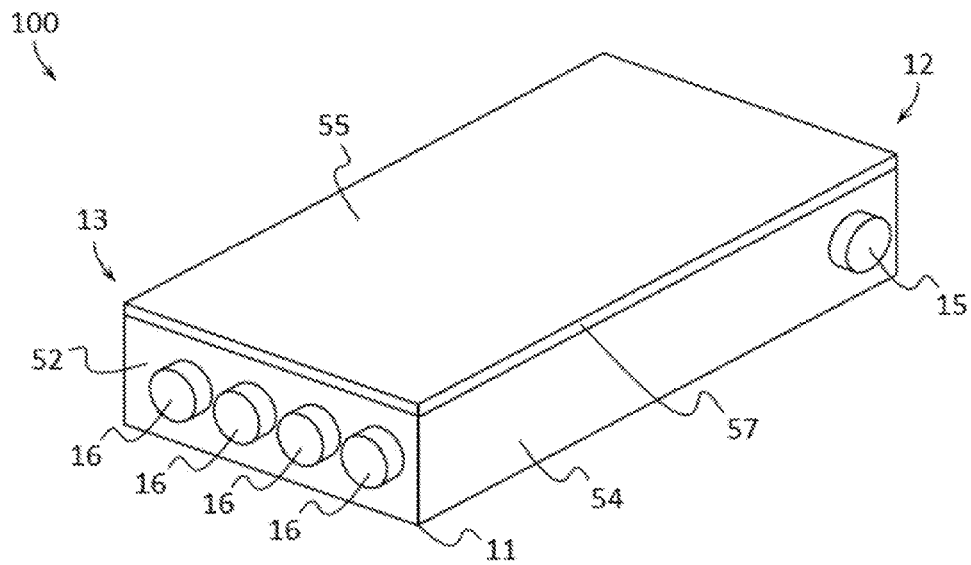
FIG. 1 depicts a top front perspective view of an example of a scalable airborne pathogen removal system according to various embodiments described herein.

For purposes of description herein, the terms "upper", "top", "lower", "bottom", "left", "right", "rear", "front", "side", "vertical", "horizontal", and derivatives thereof shall relate to the invention as oriented in FIG. 1. However, one will understand that the invention may assume various alternative orientations and step sequences, except where expressly specified to the contrary. Therefore, the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

New scalable airborne pathogen removal system for removing pathogens from an airspace are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

The present invention will now be described by example and through referencing the appended figures representing preferred and alternative embodiments. FIGS. 1-7 illustrate examples of a scalable airborne pathogen removal system ("the system") 100 for removing pathogens from an airspace 200, 200A, 200B, (FIGS. 10 and 11) according to various embodiments described herein. In some embodiments, the system 100 may comprise a housing 11 having an upstream end 12 and a downstream end 13. The housing 11 may have an airspace inlet 14 at the upstream end 12 which may be configured to receive air from the airspace 200, 200A, 200B; a supplemental inlet 15 located proximate to the airspace inlet 14 at the upstream end 12 with the supplemental inlet 15 configured to receive supplemental air; and an airspace outlet 16 configured to communicate air from the housing 11 into the airspace 200, 200A, 200B. A treatment chamber 20 within the housing 11 may be in fluid communication with the airspace inlet 14, supplemental inlet 15, and said airspace outlet 16. A second baffle 41 may be positioned at the upstream end 12 of the housing 11 between the airspace inlet 14 and the treatment chamber 20. Supplemental air from the supplemental inlet 15 may be communicated into the treatment chamber 20 through the second baffle 41. An ultraviolet light 21 may be disposed within the treatment chamber 20. An air motivator 22 may be positioned between the treatment chamber 11 and the airspace outlet 16 at the downstream end 13 of the housing which may be configured to pull air from the airspace inlet 14 and supplemental inlet 15 through the treatment chamber 11 and out of the system through an airspace outlet.

Figure 2:
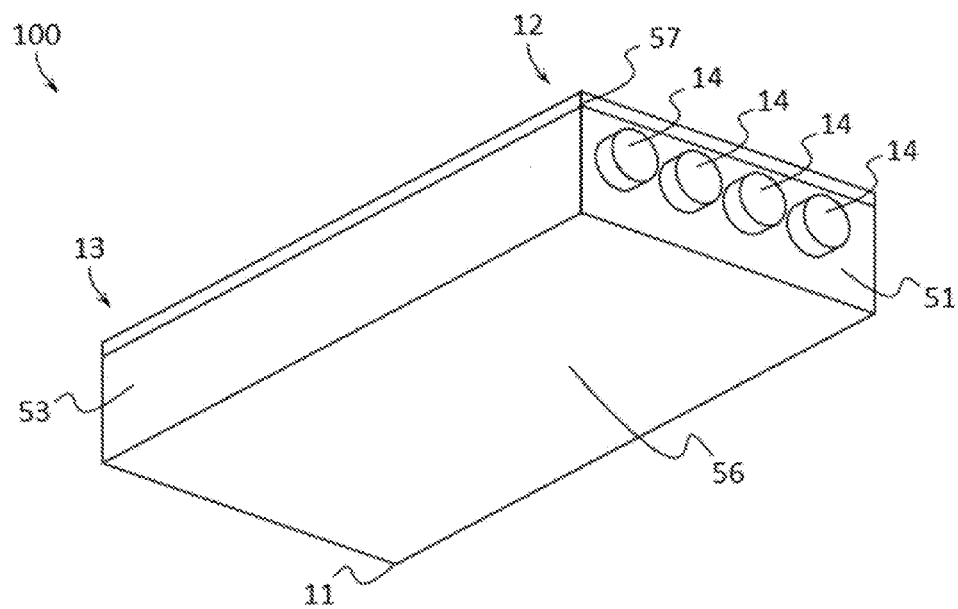
FIG. 2 illustrates a bottom rear perspective view of an example of a scalable airborne pathogen removal system according to various embodiments described herein.
Figure 8:
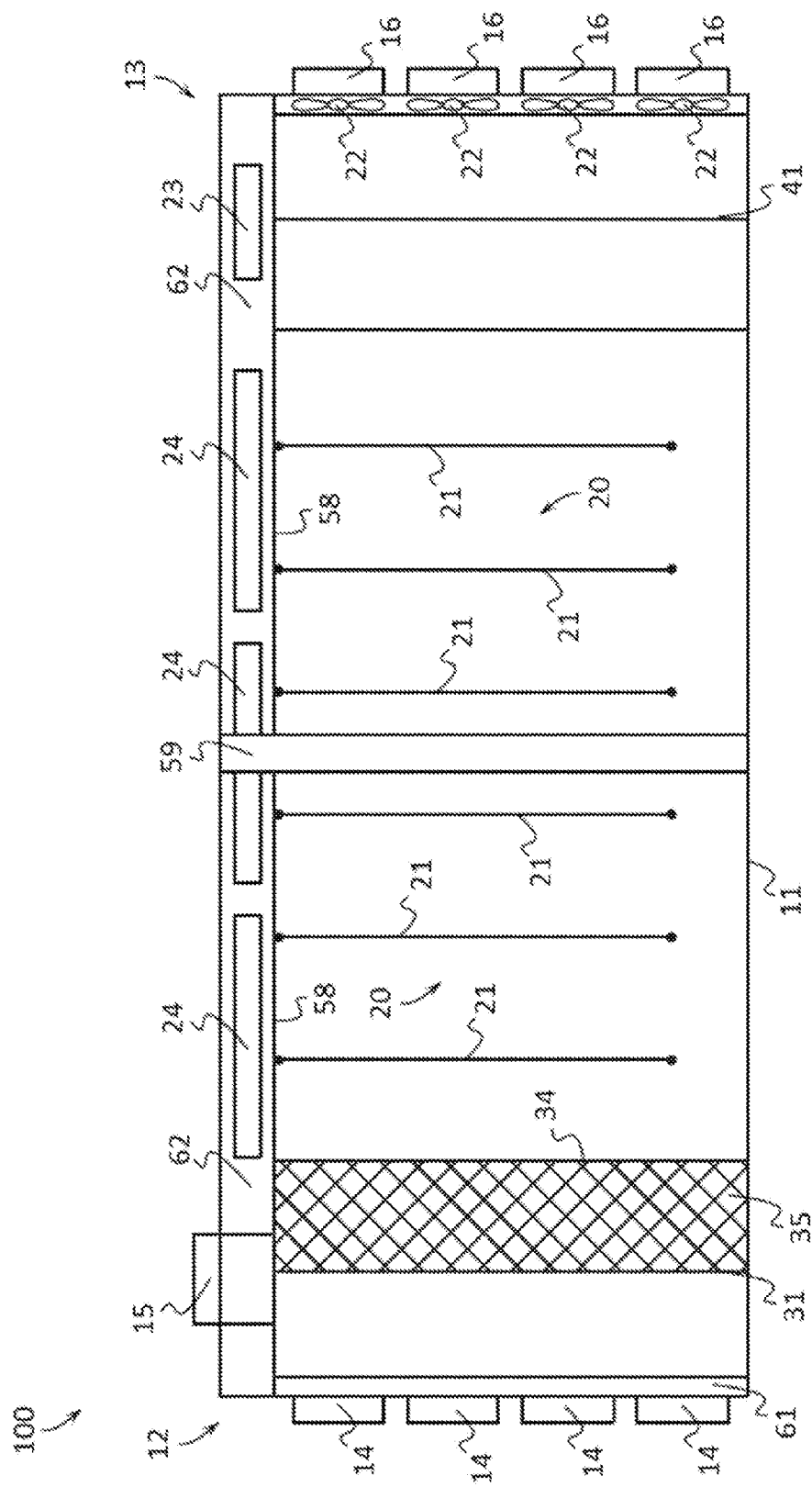
FIG. 8 illustrates a top plan view of the interior of an example of a scalable airborne pathogen removal system according to various embodiments described herein.
Figure 9:
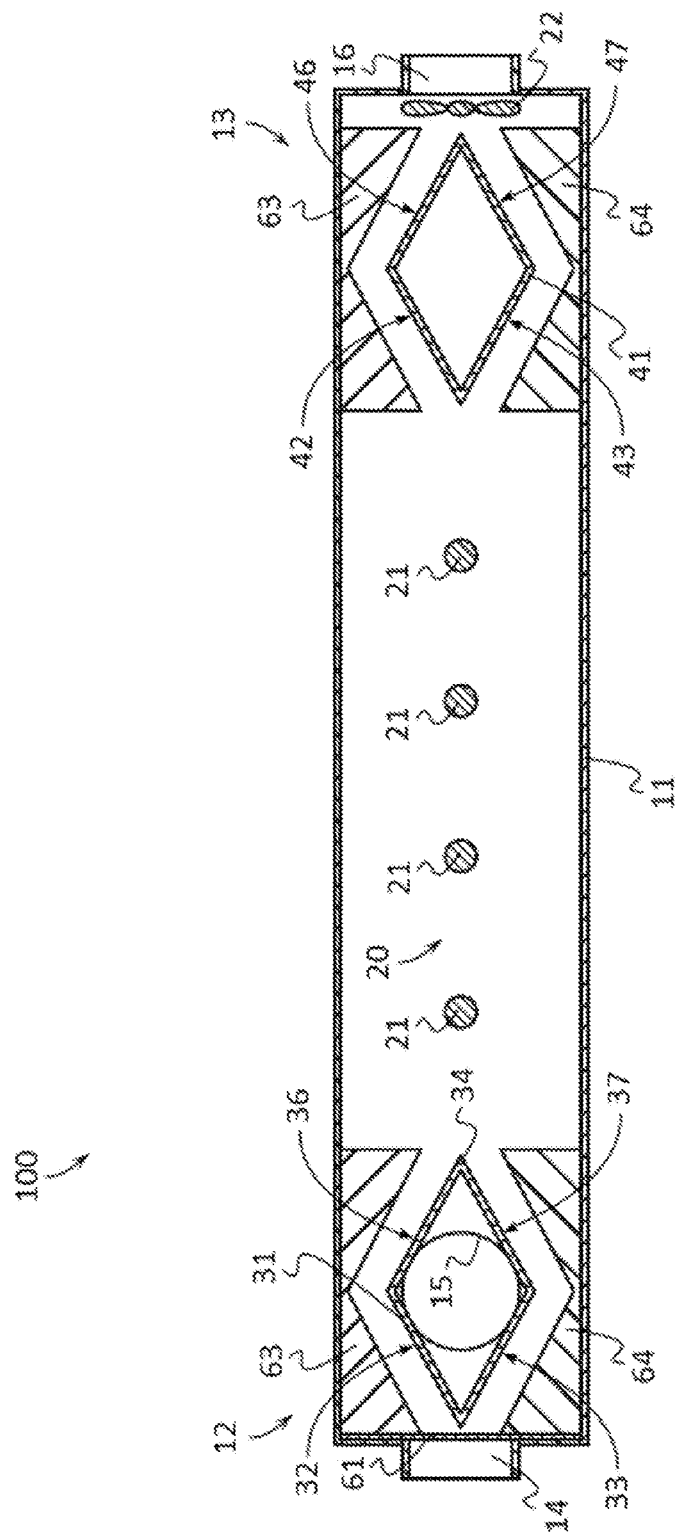
FIG. 9 shows a sectional, through line 9-9 shown in FIG. 6, elevation view of an example of a scalable airborne pathogen removal system according to various embodiments described herein.

As perhaps best shown by FIGS. 1 and 2, in some embodiments, the housing 11 may comprise a rectangular prism shape. The housing 11 may be formed by a first 51 and second 52 minor wall which may be coupled to a first 53 and second 54 elongate wall and also to a first 55 and second 56 major elongate wall. The housing may be made from materials, such as sheet metal, thereby allowing all or portions of one or more walls 51, 52, 53, 54, 55, 56, to form portions of the treatment chamber 20 and other elements disposed within the interior of the system 100 as shown in FIGS. 8 and 9. In alternative embodiments, the housing 11 may comprise or be formed by any number, size, and shaped walls. Optionally, the housing 11 may comprise one or more braces 59 (FIG. 8) which may provide structural reinforcement to the housing 11. It should be understood to one of ordinary skill in the art that the housing 11 may be configured in a plurality of sizes and shapes including "T" shaped, square shaped, rectangular shaped, cylinder shaped, cuboid shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

In some embodiments, the housing 11 may comprise a lid 57 (FIGS. 1 and 2), or other removable covering, door, access panel, and the like, which may be removably coupled to the another portion or element of the housing 11. A lid 57 may allow access to the interior of the system 100 and any element within the system 100, such as an ultraviolet light 21 and an air motivator 22.

Turning now to FIGS. 2, 4-11, the system 100 may comprise one or more airspace inlets 14 which may be configured to allow air, such as air communicated from an airspace 200, 200A, 200B, (FIGS. 10 and 11) and into the housing 11. An airspace inlet 14 may form an opening in the upstream end 12 of the housing 11, such as through a first minor wall 51. In some embodiments, an airspace inlet 14 may comprise a cylindrical shape. In other embodiments, an airspace inlet 14 may comprise a cuboid shape, triangular prism shape, or any other shape which may allow air to pass into the housing 11. Scalability of the system 100 may be increased by increasing the number and/or size of the airspace inlets 14, while scalability of the system 100 may be decreased by decreasing the number and/or size of the airspace inlets 14. In further embodiments, the system 100 may comprise a flow damper, such as a valve or plate, which stops or regulates the flow of air through an airspace inlet 14 and into the housing 11.

Referring to FIGS. 1, 3, 6-11, the system 100 may comprise one or more supplemental inlets 15 which may be configured to allow air, such as air communicated from an area outside of an airspace 200, 200A, 200B, (FIGS. 10 and 11) and into the housing 11. A supplemental inlet 15 may form an opening in the upstream end 12 of the housing 11, proximate to an airspace inlet 14 such as through a first elongate wall 53. In some embodiments, a supplemental inlet 15 may comprise a cylindrical shape. In other embodiments, a supplemental inlet 15 may comprise a cuboid shape, triangular prism shape, or any other shape which may allow air to pass into the housing 11. Scalability of the system 100 may be increased by increasing the number and/or size of the supplemental inlets 15, while scalability of the system 100 may be decreased by decreasing the number and/or size of the supplemental inlets 15. In further embodiments, the system 100 may comprise a flow damper, such as a valve or plate, which stops or regulates the flow of air through a supplemental inlet 15 and into the housing 11.

Figure 10:
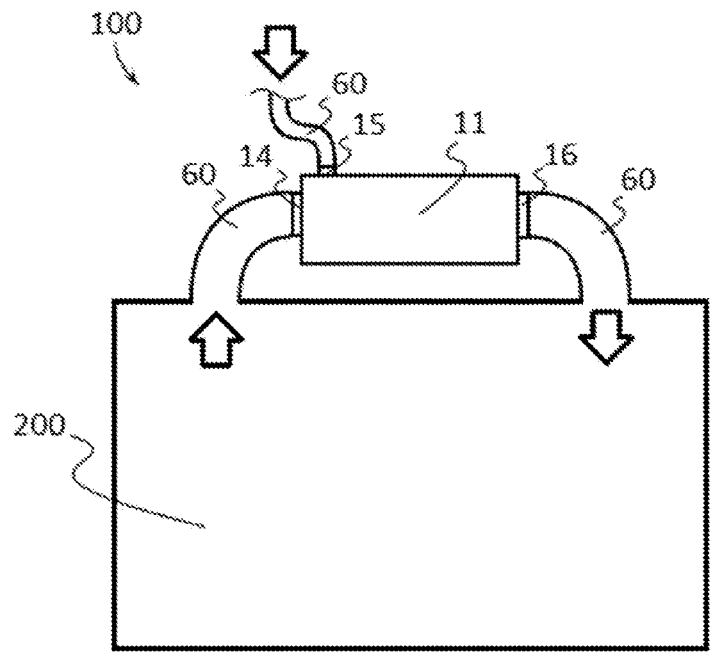
FIG. 10 depicts a block diagram of an example of a scalable airborne pathogen removal system in communication with an exemplary airspace according to various embodiments described herein.
Figure 11:
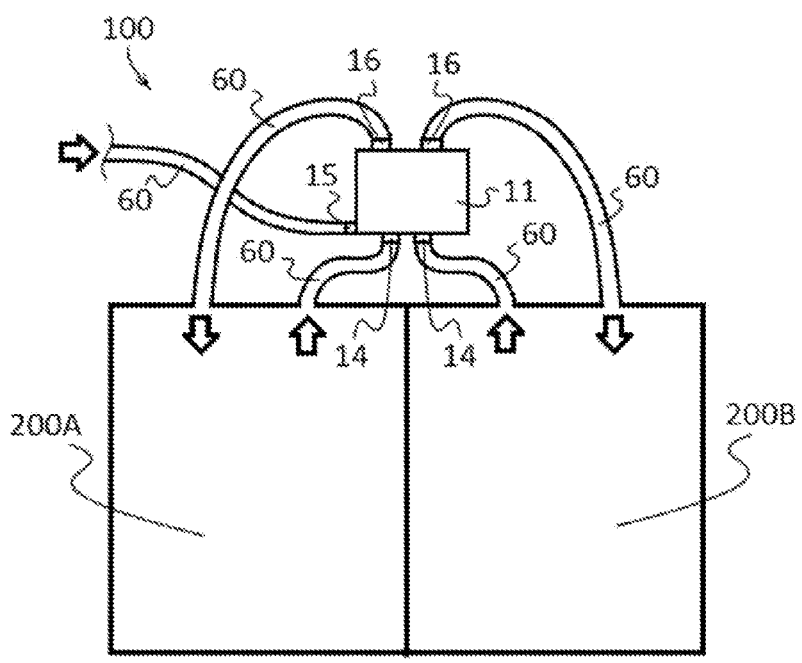
FIG. 11 illustrates a block diagram of an example of a scalable airborne pathogen removal system in communication with a first exemplary airspace and a second exemplary airspace according to various embodiments described herein.

As shown in FIGS. 1, 4, 7-11, the system 100 may comprise one or more airspace outlets 16 which may be configured to allow air, such as air communicated from the treatment chamber 20 to be communicated out of the housing 11 and into an airspace 200, 200A, 200B, (FIGS. 10 and 11). An airspace outlet 16 may form an opening in the downstream end 13 of the housing 11, such as through a second minor wall 52. In some embodiments, an airspace outlet 16 may comprise a cylindrical shape. In other embodiments, an airspace outlet 16 may comprise a cuboid shape, triangular prism shape, or any other shape which may allow air to pass out of the housing 11. Scalability of the system 100 may be increased by increasing the number and/or size of the airspace outlets 16, while scalability of the system 100 may be decreased by decreasing the number and/or size of the airspace outlets 16. In further embodiments, the system 100 may comprise a flow damper, such as a valve or plate, which stops or regulates the flow of air through an airspace outlet 16 and out of the housing 11.

Figure 3:
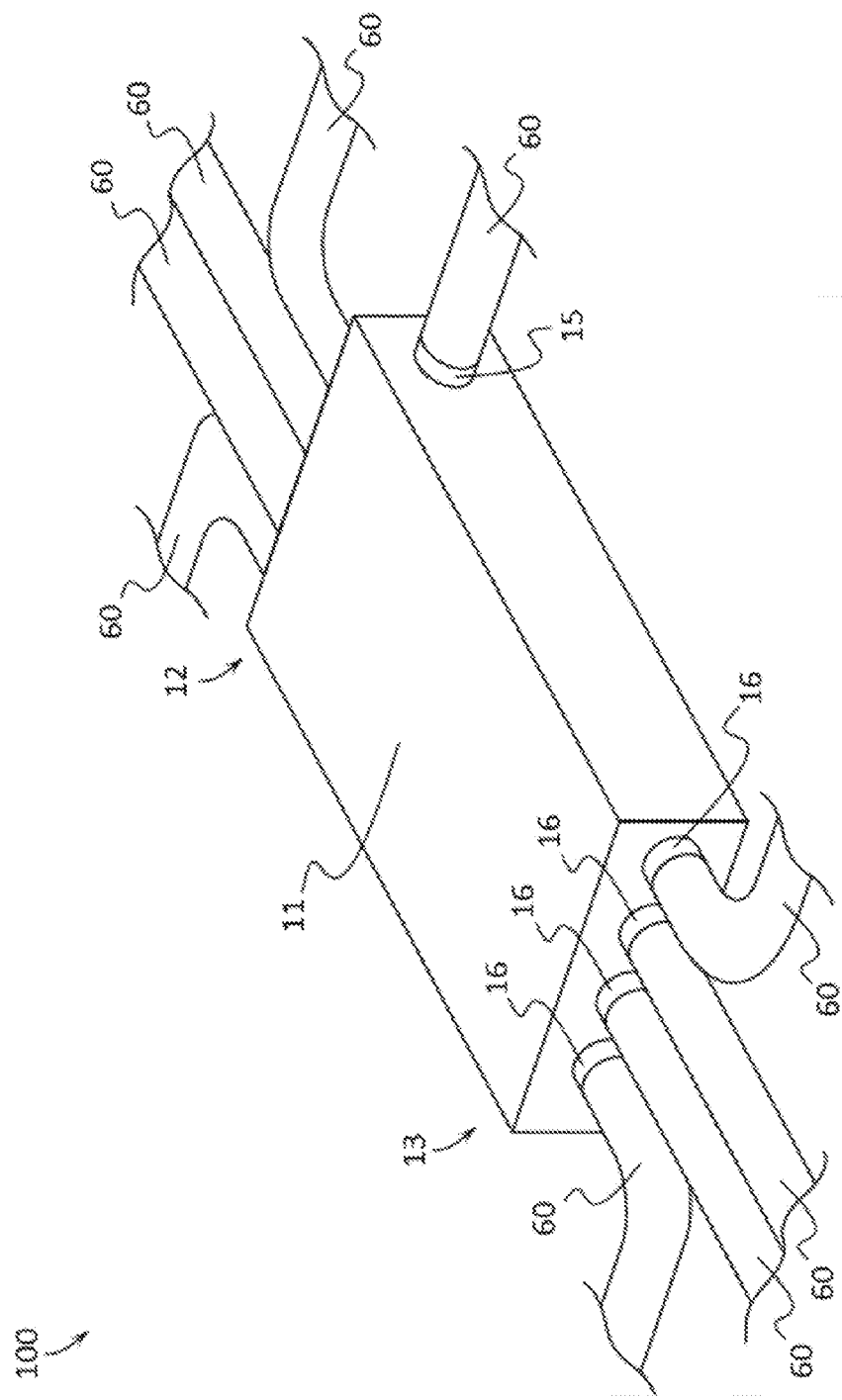
FIG. 3 shows a rear top perspective view of an example of a scalable airborne pathogen removal system comprising flexible air ducts according to various embodiments described herein.
Figure 4:
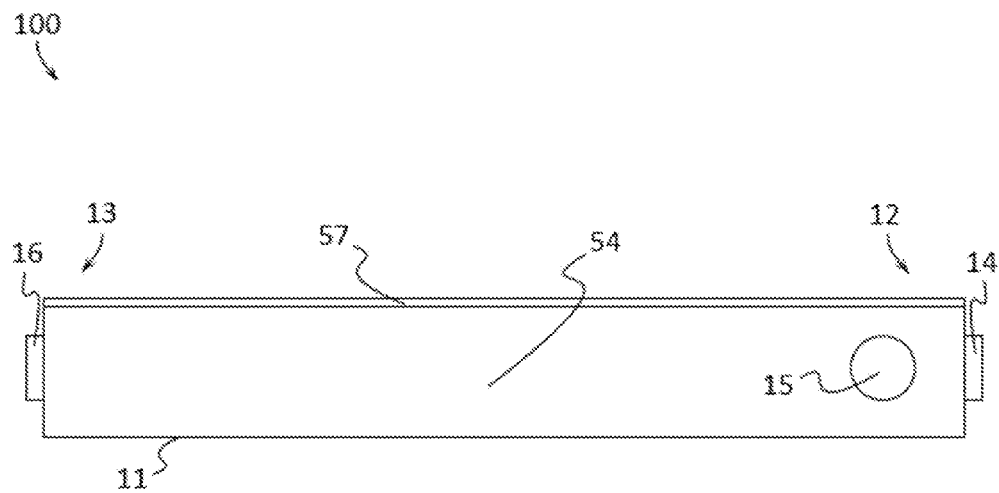
FIG. 4 depicts an elevation view of the side of an example of a scalable airborne pathogen removal system according to various embodiments described herein.
Figure 5:
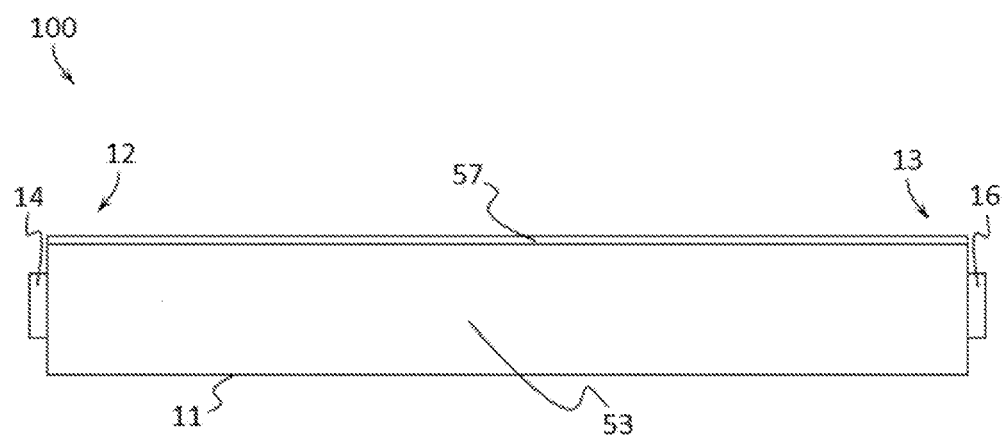
FIG. 5 illustrates an elevation view of an opposite side of an example of a scalable airborne pathogen removal system according to various embodiments described herein.
Figure 6:
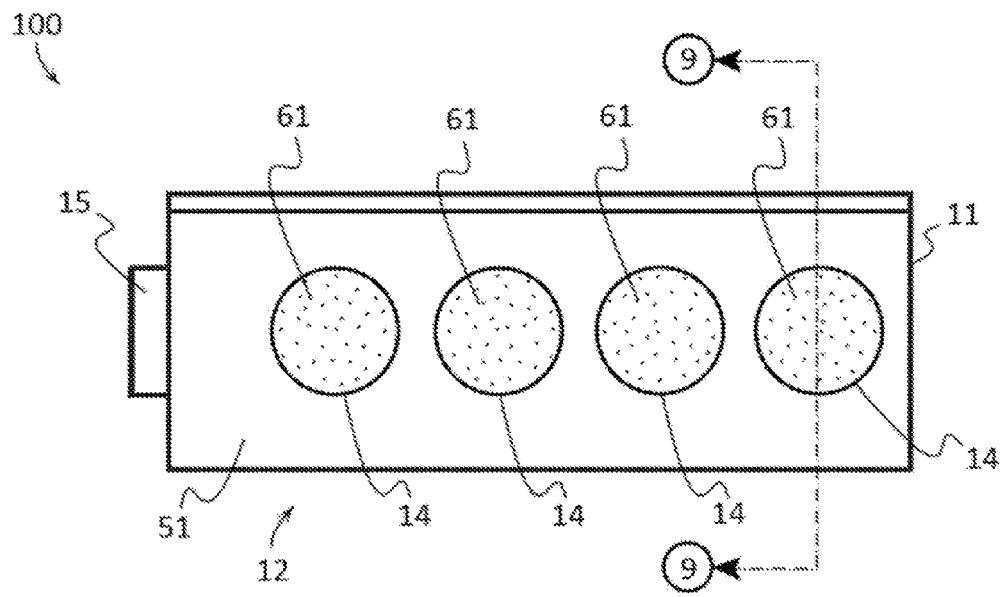
FIG. 6 shows an elevation view of an upstream end of an example of a scalable airborne pathogen removal system according to various embodiments described herein.
Figure 7:
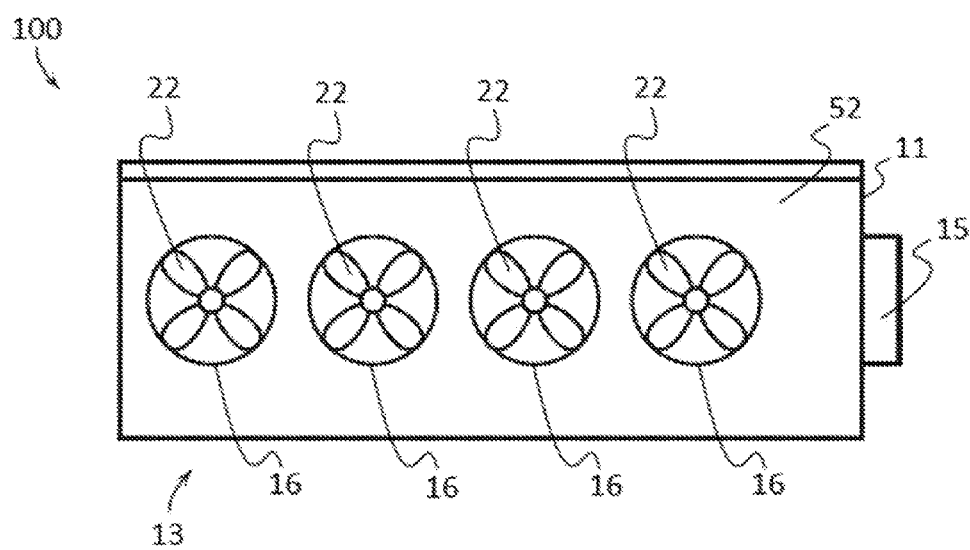
FIG. 7 depicts an elevation view of a downstream end of an example of a scalable airborne pathogen removal system according to various embodiments described herein.

As perhaps best shown in FIGS. 3, 10, and 11, in some embodiments, the system 100 may comprise one or more communication ducts 60 which may communicate air to or from the housing 11. In further embodiments, one or more communication ducts 60 may communicate air from an airspace 200, 200A, 200B, (FIGS. 10 and 11) to one or more airspace inlets 14. In further embodiments, one or more communication ducts 60 may communicate air from outside an airspace 200, 200A, 200B, to one or more supplemental inlets 15. In still further embodiments, one or more communication ducts 60 may communicate air from one or more airspace outlets 16 to an airspace 200, 200A, 200B. For example, the system 100 may comprise a first airspace inlet 14, a second airspace inlet 14, a first airspace outlet 16, a second airspace outlet 16, and a supplemental inlet 15 with a first communication duct 60 coupled to the first airspace inlet 14, a second communication duct 60 coupled to the second airspace inlet 14, a third communication duct 60 coupled to the first airspace outlet 16, a fourth communication duct 60 coupled to the second airspace outlet 16, and a fifth communication duct 60 coupled to the supplemental inlet 15.

Communication ducts 60 may be configured in various sizes and shapes, such as cylindrical shaped, rectangular prism shaped, or any other suitable shape for communicating air. Additionally, all or portions of a communication duct 60 may be rigid and/or flexible and be formed from or comprise metal, plastic, fiberglass, composite materials, or any other suitable material. Scalability of the system 100 may be increased by increasing the number and/or size of the communication ducts 60, while scalability of the system 100 may be decreased by decreasing the number and/or size of the communication ducts 60. Optionally, air diffusers or other air directing devices may be coupled to the ends of one or more ducts 60 preferably where a duct 60 is coupled to an airspace 200, 200A, 200B, (FIGS. 10 and 11). Air diffusers and the like may be either manual or automatic and formed of any material customarily utilized. Furthermore, air diffusers and the like may be of any size and shape suitable for the scale of the installation. Preferably, duct holding and shaping devices may be used to install and position the communication ducts 60 at proper angels and curves to prevent blockages and other malfunctions with one or more hanging devices or fasteners of proper strength and rating which may be used to install the housing 11, communication ducts 60, or any other elements of the system 100.

In some embodiments, the system 100 may comprise one or more filters 61 (FIGS. 6, 8, and 9) which may be configured to remove particulate matter from air entering, passing through, and/or exiting the housing 11. In some embodiments, a filter 61 may be positioned within the housing 11 proximate to one or more of the airspace inlets 14 so that air entering the housing 11 through the airspace inlets 14 is filtered before contacting a first baffle 31 and therefore before entering the treatment chamber 20. In further embodiments, a filter 61 may be positioned within the housing 11 proximate to one or more of the airspace outlets 16 so that air that has passed through the treatment chamber 20 may be filtered before exiting the housing 11 through an airspace outlet 16. In still further embodiments, a filter 61 may be positioned within the housing 11 proximate to one or more of the supplemental inlets 15 so that air entering the housing 11 through a supplemental inlet 15 is filtered before entering the treatment chamber 20.

A filter 61 may comprise a MERV 6 type air filter in some embodiments. In other embodiments, a filter 61 may comprise any other type of air filter which may be used to filter particulate matter from air. Scalability of the system 100 may be increased by increasing the number and/or size of the filters 61, while scalability of the system 100 may be decreased by decreasing the number and/or size of the filters 61.

In some embodiments, an air motivator 22 may comprise a fan, blower, turbine, or other air moving device which may preferably be operated by an electric motor. In further embodiments, an air motivator 22 may comprise one or more such as a bank of fans or blowers which may be operated by one or more motors. An air motivator 22 may be positioned at the downstream end 13 of the housing 11 proximate to the airspace outlets 16. By positioning one or more air motivators 22 between the treatment chamber 20 and the airspace outlet(s) 16, the air motivators 22 may be configured to pull air from the airspace inlet(s) 14 and supplemental inlet(s) 15 through the treatment chamber 20. Scalability of the system 100 may be increased by increasing the number, size, and/or power of the air motivators 22, while scalability of the system 100 may be decreased by decreasing the number, size, and/or power of the air motivators 22.

In some embodiments, the system 100 may comprise one or more utility compartments 62 (FIG. 8) which may be used to contain and/or sequester one or more electronic elements from the treatment chamber 20 and/or from air passing through the housing 11. In further embodiments, a utility compartment 62 may be formed by a utility wall 58, which may be coupled to the interior of the housing 11. Electronic elements, such as a power supply 23, light control module 24, processing unit 25, and/or any other element may be positioned within the utility compartment 62 thereby containing and/or sequestering one or more electronic elements from the treatment chamber 20 and/or from air passing through the housing 11.

The system 100 may comprise one or more treatment chambers 20 (FIGS. Band 9) within the housing 11. A treatment chamber 20 may be in fluid communication with the airspace inlets 14, supplemental inlets 15, and airspace outlets 16 so that air may be introduced to the treatment chamber 20 through the airspace inlets 14 and/or supplemental inlets 15 and removed from the treatment chamber 20 through the airspace outlets 16. In some embodiments, portions of a treatment chamber 20 may be formed by portions of the housing 11 such as by one or more of the first 51 and second 52 minor walls, first 53 and second 54 elongate walls, first 55 and second 56 major elongate walls, lid 57 (FIGS. 1 and 2), and/or utility wall 58. Preferably portions of the housing 11 which form the treatment chamber 20 may covered in or comprise an Ultraviolet (UV) light reflecting material. For example, portions of the housing 11 which form the treatment chamber 20 may comprise an UV light reflecting material such as reflective or polished steel, aluminum, or other material. In another example, portions of the housing 11 which form the treatment chamber 20 may comprise an UV light reflecting material such as mirrors, mirror coatings, chrome coatings, reflective paints, or any other suitable UV light reflecting method. Scalability of the system 100 may be increased by increasing the number and/or size of the treatment chamber 20, while scalability of the system 100 may be decreased by decreasing the number and/or size of the treatment chamber 20.

Figure 12:
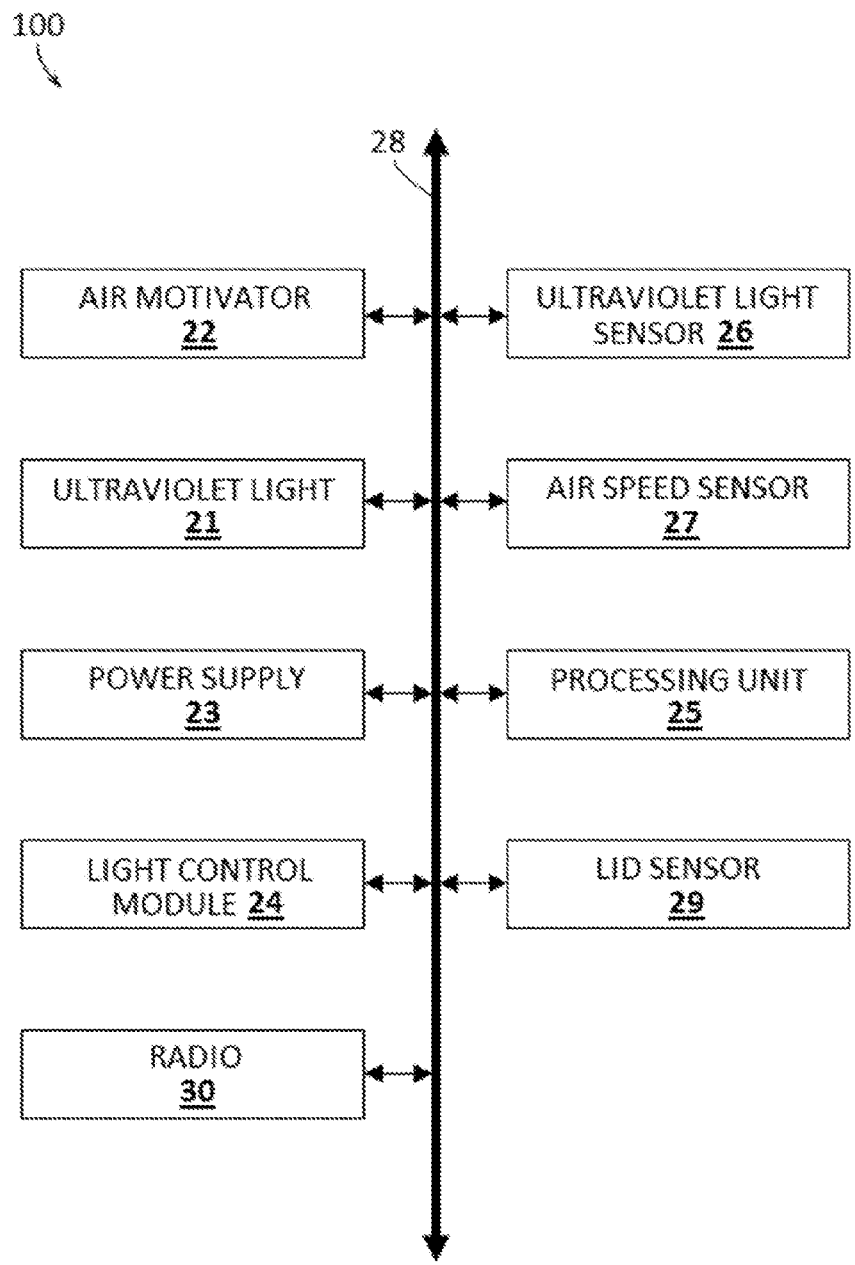
FIG. 12 shows a block diagram of some electrical elements of an example of a scalable airborne pathogen removal system according to various embodiments described herein.

Turning now to FIGS. 8, 9, 12, in some embodiments, the system 100 may comprise one or more ultraviolet (UV) lights 21 which may be positioned within the treatment chamber 20 and which may provide Ultraviolet germicidal irradiation (UVGI). In further embodiments, one or more UV lights 21 may be positioned anywhere within the system 100. The term "ultraviolet (UV) light" should be understood to include any source of man-made UV light technology including lamps, LEDs, and types such as 2-pin, 4-pin, screw-in, T5 bi-pin, plug-in compact, etc. In preferred embodiments, a UV light 21 may emit Ultraviolet C (UVC) with a wavelength of approximately 100-280 nanometers. Scalability of the system 100 may be increased by increasing the number, size, and/or power of the UV lights 21, while scalability of the system 100 may be decreased by decreasing the number, size, and/or power of the UV lights 21.

As perhaps best shown by FIGS. 8 and 9, the system 100 may comprise a first baffle 31 positioned at the upstream end 12 of the housing 11 between the airspace inlet(s) 14 and the treatment chamber 20. Supplemental air from the supplemental inlet(s) 15 may be communicated into the treatment chamber 20 through the first baffle 31. In further embodiments, the system 100 may comprise a second 41 baffle positioned at the downstream end 13 of the housing 11 between the treatment chamber 20 and the air motivator(s) 22.

In some embodiments, the first baffle 31 may comprise a diamond prism shape, when viewed in cross section as shown in FIG. 8, which may extend across the housing 11 such as from a first elongate wall 53 to a second elongate wall 54 or from a first 53 or second 54 elongate wall to a utility wall 58. In other embodiments, the first baffle 31 may comprise any other shape. It should be understood to one of ordinary skill in the art that the first baffle 31 may be configured in a plurality of sizes and shapes including rectangular prism shaped, cylinder shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

In some embodiments, the first baffle 31 may comprise a first upper incidence surface 32 coupled to a first lower incidence surface 33 with the first upper incidence surface 32 and the first lower incidence surface 33 positioned between the airspace inlet(s) 14 and the supplemental inlet(s) 15. Preferably the first upper incidence surface 32 and/or the first lower incidence surface 33 may be flat planar or curved planar in shape. In further embodiments, the first upper incidence surface 32 may be angularly coupled to the first lower incidence surface 33 at an angle between 20 and 70 degrees.

In some embodiments, the first baffle 31 may comprise a first trailing assembly 34 and supplemental air from the supplemental inlet(s) 15 may be communicated into the treatment chamber 20 through the first trailing assembly 34. The trailing assembly 34 may be coupled to the first upper incidence surface 32 and/or the first lower incidence surface 33 to form a channel or cavity into which the supplemental air may first enter before being communicated to the treatment chamber 20. A first trailing assembly 34 may be configured in any shape when viewed in cross section as shown in FIG. 8, which may extend across the housing 11 such as from a first elongate wall 53 to a second elongate wall 54 or from a first 53 or second 54 elongate wall to a utility wall 58.

In further embodiments, the first trailing assembly 34 may comprise at least one supplemental air aperture 35 which may be configured to communicate supplemental air from the supplemental inlet(s) 15 into the treatment chamber 20. A supplemental air aperture 35 may comprise a hole or other opening through which air may pass that extends through the first trailing assembly 34. In preferred embodiments, the first upper incidence surface 32, the first lower incidence surface 33, first trailing assembly 34, and/or any other component of the first baffle 31 may comprise or be coated with a dark non-reflective material to prevent UV light from escaping from the housing 11.

In still further embodiments, the first trailing assembly 34 may comprise a first upper trailing surface 36 and a first lower trailing surface 37, and both the first upper trailing surface 36 and first lower trailing surface 37 comprise a plurality of supplemental air apertures 35 configured to communicate supplemental air from the supplemental inlet(s) 15 into the treatment chamber 20. For example the first trailing assembly 34, first upper trailing surface 36, and/or first lower trailing surface 37 may be formed from a mesh material such as a metal mesh comprising a diamond cross hatching pattern forming a plurality of supplemental air apertures 35. Preferably, the first upper trailing surface 36 may be angularly coupled to the first lower trailing surface 37 at an angle between 20 and 70 degrees. In even further embodiments air pulled through airspace inlet(s) 14 may be directed over the first baffle 31 by the first upper incidence surface 32 or under the first lower incidence surface 33 where it may mix with supplemental air from supplemental inlet(s) 15 as it passed over the first upper trailing surface 36 or under the first lower trailing surface 37 into the treatment chamber.

In some embodiments, the second baffle 41 may comprise a diamond prism shape, when viewed in cross section as shown in FIG. 8, which may extend across the housing 11 such as from a first elongate wall 53 to a second elongate wall 54 or from a first 53 or second 54 elongate wall to a utility wall 58. In other embodiments, the second baffle 41 may comprise any other shape. It should be understood to one of ordinary skill in the art that the second baffle 41 may be configured in a plurality of sizes and shapes including rectangular prism shaped, cylinder shaped, hexagonal prism shaped, triangular prism shaped, or any other geometric or non-geometric shape, including combinations of shapes. It is not intended herein to mention all the possible alternatives, equivalent forms or ramifications of the invention. It is understood that the terms and proposed shapes used herein are merely descriptive, rather than limiting, and that various changes, such as to size and shape, may be made without departing from the spirit or scope of the invention.

In some embodiments, the second baffle 41 may comprise a second upper incidence surface 42, a second lower incidence surface 43, a second upper trailing surface 46 and a second lower trailing surface 47. In further embodiments, the second upper incidence surface 42 may be angularly coupled to the second lower incidence surface 43 at an angle between 20 and 70 degrees and the second upper trailing surface 46 may be angularly coupled to the second lower trailing surface 47 at an angle between 20 and 70 degrees. In still further embodiments, the second upper incidence surface 42, the second lower incidence surface 43, second upper trailing surface 46, and/or second lower trailing surface 47 may be flat planar or curved planar in shape. In even further embodiments air pulled from the treatment chamber 20 may be directed over the second baffle 41 by the second upper incidence surface 42 or under the second lower incidence surface 43 and then over the second upper trailing surface 46 or under the second lower trailing surface 47 by the air motivators 22.

Optionally, the system 100 may comprise an upper air restrictor 63. In some embodiments, an upper air restrictor 63 may be configured to be complementary in shape to portions of the first baffle 31, such as to the first upper incidence surface 32 and/or first upper trailing surface 36. An upper air restrictor 63 may be positioned above the first baffle 31 thereby constricting air passing over the baffle 31 and increasing the velocity of the air. In further embodiments, an upper air restrictor 63 may be configured to be complementary in shape to portions of the second baffle 41, such as to the second upper incidence surface 42 and/or second upper trailing surface 46. An upper air restrictor 63 may be positioned above the second baffle 41 thereby constricting air passing over the baffle 41 and increasing the velocity of the air.

Optionally, the system 100 may comprise a lower air restrictor 64. In some embodiments, a lower air restrictor 64 may be configured to be complementary in shape to portions of the first baffle 31, such as to the first lower incidence surface 33 and/or first lower trailing surface 37. A lower air restrictor 64 may be positioned below the first baffle 31 thereby constricting air passing under the baffle 31 and increasing the velocity of the air. In further embodiments, a lower air restrictor 64 may be configured to be complementary in shape to portions of the second baffle 41, such as to the second lower incidence surface 43 and/or second lower trailing surface 47. A lower air restrictor 64 may be positioned below the second baffle 41 thereby constricting air passing under the baffle 41 and increasing the velocity of the air.

FIG. 10 depicts a block diagram of an example of a scalable airborne pathogen removal system 100 in communication with an exemplary airspace 200 according to various embodiments described herein. In this example, the system 100 comprises a first communication duct 60 which is communicating air from the airspace 200 and into the airspace inlet 14. A second communication duct 60 is communicating supplemental air from outside of the airspace 200 into a supplemental inlet 15. The air then is pulled through the housing 11 by one or more air motivators 22 and then out of the housing 11 through an airspace outlet 16. The airspace outlet 16 is in communication with a third communication duct 60 which is configured to return the air into the airspace 200. In preferred embodiments, the supplemental air communicated by the supplemental inlet 15 may be communicated from outside of the airspace 200, such as from outside of the building that is forming the airspace 200. In this manner fresh air provided by a supplemental inlet 15 may be used to dilute the amount of carbon dioxide or to increase the amount of oxygen in the airspace 200.

FIG. 11 illustrates a block diagram of an example of a scalable airborne pathogen removal system 100 in communication with a first exemplary airspace 200A and a second exemplary airspace 200B according to various embodiments described herein. In this example, the system 100 comprises a first communication duct 60 which is communicating air from the first airspace 200A into a first airspace inlet 14 and a second communication duct 60 which is communicating air from the second airspace 200B into a second airspace inlet 14. A third communication duct 60 is communicating supplemental air from outside of the airspaces 200A, 200B, into a supplemental inlet 15. The air then is pulled through the housing 11 by one or more air motivators 22 and then out of the housing 11 through a first airspace outlet 16 and a second airspace outlet 16. The first airspace outlet 16 is in communication with a fourth communication duct 60 which is configured to return the air into the first airspace 200A and the second airspace outlet 16 is in communication with a fifth communication duct 60 which is configured to return the air into the second airspace 200B. In preferred embodiments, the supplemental air communicated by the supplemental inlet 15 may be communicated from outside of the airspaces 200A, 200B, such as from outside of the building that is forming the airspaces 200A, 200B. In this manner fresh air provided by a supplemental inlet 15 may be used to dilute the amount of carbon dioxide or to increase the amount of oxygen in the airspaces 200A, 200B.

FIG. 12 shows a block diagram of some electrical elements of an example of a scalable airborne pathogen removal system 100 according to various embodiments described herein. In some embodiments, the system 100 may comprise a processing unit 25 in electrical communication with the air motivator(s) 22 and UV lights 21. A processing unit 25 may comprise a processor, input/output (I/O) interfaces, and memory. Generally, a processing unit 25 may execute functions of one or more electrical elements of the system 100 based on software or rules engines contained in the memory. In further embodiments, the processing unit 25 may be in electrical communication with one or more light control modules 24, power supplies 23, UV light sensors 26, air speed sensors 27, and/or radio 30. Electrical communication may be provided by a local bus 28 which may be formed by one or more wires, circuit boards, and the like. Electrical power may be received by the power supply 23 and converted to a form suitable for powering each of the electrical elements.

In some embodiments, the system 100 may comprise one or more UV light sensors 26 which may be configured to signal the processing unit 25 that one or more UV lights 21 have stopped functioning or are in need of service. A UV light sensor 26 may comprise a voltage sensor, photo sensor, or any other suitable sensor for detecting if an UV light 21 has stopped functioning or are in need of service.

In some embodiments, the system 100 may comprise one or more light control modules 24. A light control module 24 may comprise any suitable device configured to operate an UV light 21. For example, an UV light 21 comprising one or more UV light emitting diodes (LED) may be operated by a microcontroller or other LED operating device, while an UV light 21 comprising one or more UV light lamps may be operated by a ballast or other suitable lamp operating device.

In some embodiments, the system 100 may comprise one or more airspeed sensors 27 which may be configured to communicate the amount or speed of air entering, passing through, and/or exiting the system 100 to the processing unit 25. An airspeed sensor 27 may comprise a thermal anemometer or any other type of sensor which may be used to measure the speed and/or volume of air proximate to or contacting the airspeed sensor 27.

In some embodiments, the system 100 may comprise one or more lid sensors 29 which may be configured to communicate if the lid 57 (FIGS. 1 and 2) or other removable covering is open, ajar, and/or closed to the processing unit 25. Preferably, if the lid 57 or other removable covering is open or ajar, the processing unit 25 may direct a light control module 24 and/or the UV lights 21 to turn off. An airspeed sensor 27 may comprise a magnetic sensor, a pressure switch, an electrical circuit, or any other method configured to detect if the lid 57 or other removable covering is open, ajar, or closed.

In some embodiments, the system 100 may comprise a radio 30 which may enable wireless communication between the processing unit 25 and an external access device or network. In some embodiments, a radio 30 may operate on a WIFI band. Any number of suitable wireless data communication protocols, techniques, or methodologies can be supported by the radio 30, including, without limitation: RF; IrDA (infrared); Bluetooth; ZigBee (and other variants of the IEEE 802.15 protocol); IEEE 802.11 (any variation); IEEE 802.16 (WiMAX or any other variation); Near-Field Communication (NFC); cellular/wireless/cordless telecommunication protocols (e.g. 3G/4G, etc.); wireless home network communication protocols; and any other protocols for wireless communication.

While some materials have been provided, in other embodiments, the elements that comprise the system 100 such as the housing 11, treatment chamber 20, first baffle 31, optional second baffle 41, and/or any other element discussed herein may be made from durable materials such as aluminum, steel, other metals and metal alloys, wood, hard rubbers, hard plastics, fiber reinforced plastics, carbon fiber, fiber glass, resins, polymers or any other suitable materials including combinations of materials. Additionally, one or more elements may be made from or comprise durable and slightly flexible materials such as soft plastics, silicone, soft rubbers, or any other suitable materials including combinations of materials. In some embodiments, one or more of the elements that comprise the system 100 may be coupled or connected together with heat bonding, chemical bonding, adhesives, clasp type fasteners, clip type fasteners, rivet type fasteners, threaded type fasteners, other types of fasteners, or any other suitable joining method. In other embodiments, one or more of the elements that comprise the system 100 may be coupled or removably connected by being press fit or snap fit together, by one or more fasteners such as hook and loop type or Velcro® fasteners, magnetic type fasteners, threaded type fasteners, sealable tongue and groove fasteners, snap fasteners, clip type fasteners, clasp type fasteners, ratchet type fasteners, a push-to-lock type connection method, a turn-to-lock type connection method, slide-to-lock type connection method or any other suitable temporary connection method as one reasonably skilled in the art could envision to serve the same function. In further embodiments, one or more of the elements that comprise the system 100 may be coupled by being one of connected to and integrally formed with another element of the system 100.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A scalable airborne pathogen removal system for removing pathogens from an airspace, the system comprising:

a housing having an upstream end with an upstream side and a downstream end with a downstream side, said housing having an airspace inlet at said upstream side configured to receive air from the airspace;

a supplemental inlet located on an elongate side of the housing, the elongate side of the housing arranged perpendicular to the upstream side, said supplemental inlet configured to receive supplemental air;

an airspace outlet configured to communicate air from the housing into the airspace;

a treatment chamber within said housing and in fluid communication with said airspace inlet, said supplemental inlet, and said airspace outlet;

a first baffle positioned at the upstream end of the housing and traversing the treatment chamber in a direction parallel to the upstream side, wherein the supplemental inlet communicates air into the treatment chamber through the first baffle;

an ultraviolet light disposed within said treatment chamber; and an air motivator configured to pull air from the airspace inlet and supplemental inlet through the treatment chamber.

2. The system of claim 1, wherein the first baffle comprises a first upper incidence surface coupled to a first lower incidence surface, and wherein the first upper incidence surface and the first lower incidence surface are positioned between the airspace inlet and the supplemental inlet.

3. The system of claim 2, wherein the first upper incidence surface is angularly coupled to the first lower incidence surface at an angle between 20 and 70 degrees.

4. The system of claim 1, wherein the first baffle comprises a first trailing assembly, and wherein supplemental air from the supplemental inlet is communicated into the treatment chamber through the first trailing assembly.

5. The system of claim 4, wherein the first trailing assembly comprises at least one supplemental air aperture, and wherein the supplemental air aperture is configured to communicate supplemental air from the supplemental inlet into the treatment chamber.

6. The system of claim 5, wherein the first trailing assembly comprises a first upper trailing surface and a first lower trailing surface, and wherein both the first upper trailing surface and first lower trailing surface comprise a plurality of supplemental air apertures configured to communicate supplemental air from the supplemental inlet into the treatment chamber.

7. The system of claim 5, wherein the first upper trailing surface is angularly coupled to the first lower trailing surface at an angle between 20 and 70 degrees.

8. The system of claim 1, further comprising a first airspace inlet, a second airspace inlet, a first airspace outlet, and a second airspace outlet.

9. The system of claim 8, further comprising a first communication duct coupled to the first airspace inlet, a second communication duct coupled to the second airspace inlet, a third communication duct coupled to the first airspace outlet, and a fourth communication duct coupled to the second airspace outlet.

10. A scalable airborne pathogen removal system for removing pathogens from an airspace, the system comprising:

a housing having an upstream end and a downstream end, said housing having an airspace inlet at said upstream end configured to receive air from the airspace, an supplemental inlet located proximate to said airspace inlet at said upstream end with said supplemental inlet configured to receive supplemental air, and an airspace outlet configured to communicate air from the housing into the airspace;

a treatment chamber within said housing and in fluid communication with said airspace inlet, said supplemental inlet, and said airspace outlet;

a first baffle positioned at the upstream end of the housing and transversely crossing the housing between the airspace inlet and the treatment chamber, wherein the supplemental air from the supplemental inlet is communicated first into the first baffle before being communicated into the treatment chamber;

an ultraviolet light disposed within said treatment chamber;

an air motivator configured to pull air from the airspace inlet and supplemental inlet through the treatment chamber; and a second baffle positioned at the downstream end of the housing between the treatment chamber and the air motivator.

11. The system of claim 10, wherein the first baffle comprises a first upper incidence surface coupled to a first lower incidence surface, and wherein the first upper incidence surface and the first lower incidence surface are positioned between the airspace inlet and the supplemental inlet.

12. The system of claim 11, wherein the second baffle comprises a second upper incidence surface angularly coupled to a second lower incidence surface.

13. The system of claim 12, wherein the first upper incidence surface is angularly coupled to the first lower incidence surface at an angle between 20 and 70 degrees, and wherein the second upper incidence surface is angularly coupled to the second lower incidence surface at an angle between 20 and 70 degrees.

14. The system of claim 10, wherein the first baffle comprises a trailing assembly, wherein supplemental air from the supplemental inlet is communicated into the treatment chamber through the trailing assembly.

15. The system of claim 14, wherein the trailing assembly comprises at least one supplemental air aperture, and wherein the supplemental air aperture is configured to communicate supplemental air from the supplemental inlet into the treatment chamber.

16. The system of claim 15, wherein the trailing assembly comprises an upper trailing surface and a lower trailing surface, and wherein both the upper trailing surface and lower trailing surface comprise a plurality of supplemental air apertures configured to communicate supplemental air from the supplemental inlet into the treatment chamber.

17. The system of claim 15, wherein the upper trailing surface is angularly coupled to the lower trailing surface at an angle between 20 and 70 degrees.

18. The system of claim 10, further comprising a first airspace inlet, a second airspace inlet, a first airspace outlet, and a second airspace outlet.

19. The system of claim 18, further comprising a first communication duct coupled to the first airspace inlet, a second communication duct coupled to the second airspace inlet, a third communication duct coupled to the first airspace outlet, and a fourth communication duct coupled to the second airspace outlet.

\* \* \* \* \*